United States Patent
Burris et al.

(10) Patent No.: US 7,244,354 B2
(45) Date of Patent: Jul. 17, 2007

(54) OZONE IRRIGATOR

(75) Inventors: W. Alan Burris, Pittsford, NY (US); Phillip M. Prinsen, Ontario, NY (US)

(73) Assignee: Alab, LLC, Rush, NY (US)

( * ) Notice: Subject to any disclaimer, the term of this patent is extended or adjusted under 35 U.S.C. 154(b) by 210 days.

(21) Appl. No.: 10/042,473

(22) Filed: Jan. 9, 2002

(65) Prior Publication Data

US 2002/0094309 A1   Jul. 18, 2002

Related U.S. Application Data

(60) Provisional application No. 60/261,415, filed on Jan. 12, 2001.

(51) Int. Cl.
  *C02F 1/40*  (2006.01)
  *B01J 19/08*  (2006.01)

(52) U.S. Cl. .............. 210/135; 210/138; 210/150; 210/194; 422/186.12; 422/186.14

(58) Field of Classification Search .......... 422/186.07, 422/186.11, 305, 112, 186.12, 186.14; 210/150, 210/151, 188, 138, 194, 132, 135, 137, 748
See application file for complete search history.

(56) References Cited

U.S. PATENT DOCUMENTS

| | | | |
|---|---|---|---|
| 3,590,813 A | 7/1971 | Roszyk | 128/66 |
| 3,811,432 A | 5/1974 | Moret | 128/66 |
| 3,820,532 A | 6/1974 | Eberhardt et al. | 128/66 |
| 4,094,311 A | 6/1978 | Hudson | 128/66 |
| 4,108,167 A | 8/1978 | Hickman et al. | 128/66 |
| 4,141,352 A | 2/1979 | Ebner et al. | 128/62 A |
| 4,229,634 A | 10/1980 | Hickman et al. | 200/302 |
| 4,302,186 A | 11/1981 | Cammack et al. | 433/80 |
| 4,411,652 A | 10/1983 | Kramer et al. | 604/153 |
| 4,422,450 A | 12/1983 | Rusteberg | 128/62 A |
| 4,459,269 A | 7/1984 | Zackay et al. | 423/219 |
| 4,555,335 A | 11/1985 | Burris | 210/192 |
| 4,958,629 A | 9/1990 | Peace et al. | 128/66 |
| 4,979,503 A | 12/1990 | Chermack | 128/66 |
| 4,989,590 A | 2/1991 | Baum et al. | 128/66 |
| 5,207,993 A * | 5/1993 | Burris | 422/256 |
| 5,213,773 A | 5/1993 | Burris | 422/256 |
| 5,422,043 A | 6/1995 | Burris | 261/122.1 |
| 5,529,760 A | 6/1996 | Burris | 422/186.07 |
| 5,846,418 A | 12/1998 | Thompson et al. | 210/266 |
| 5,858,283 A | 1/1999 | Burris | 261/122.1 |
| 5,993,402 A | 11/1999 | Sauer et al. | 601/162 |
| 6,343,779 B1 | 2/2002 | Morita | |
| 6,348,155 B1 | 2/2002 | Conway et al. | |

* cited by examiner

*Primary Examiner*—Thao T. Tran
(74) *Attorney, Agent, or Firm*—Duane C. Basch; Basch + Nickerson LLP

(57) ABSTRACT

This portable appliance can be used to clean teeth by liquid (water or solution) containing dissolved ozone, which is a potent oxidizer and germ killer. Preferably, its cleaning action is enhanced by pulsations of the liquid stream. The dissolved ozone can reduce or eliminate gingivitis, gum bleeding, bad breath, teeth stains, and harmful oral bacteria. This appliance can also be used for nasal irrigation for sinusitis treatment and for ear irrigation, eye care, and general cleaning. Additionally, since its output pump is independent of the ozone dissolving system, the ozone dissolving system can be configured as an add on device for an oral irrigator such as a Water Pik™ manufactured by WaterPik Technologies, Inc. In this configuration, the ozonated liquid is delivered by either gravity or pumped flow, to the original reservoir connection with the irrigator serving as the delivery portion of this invention.

32 Claims, 6 Drawing Sheets

2 liquid pump system

Diffuser System

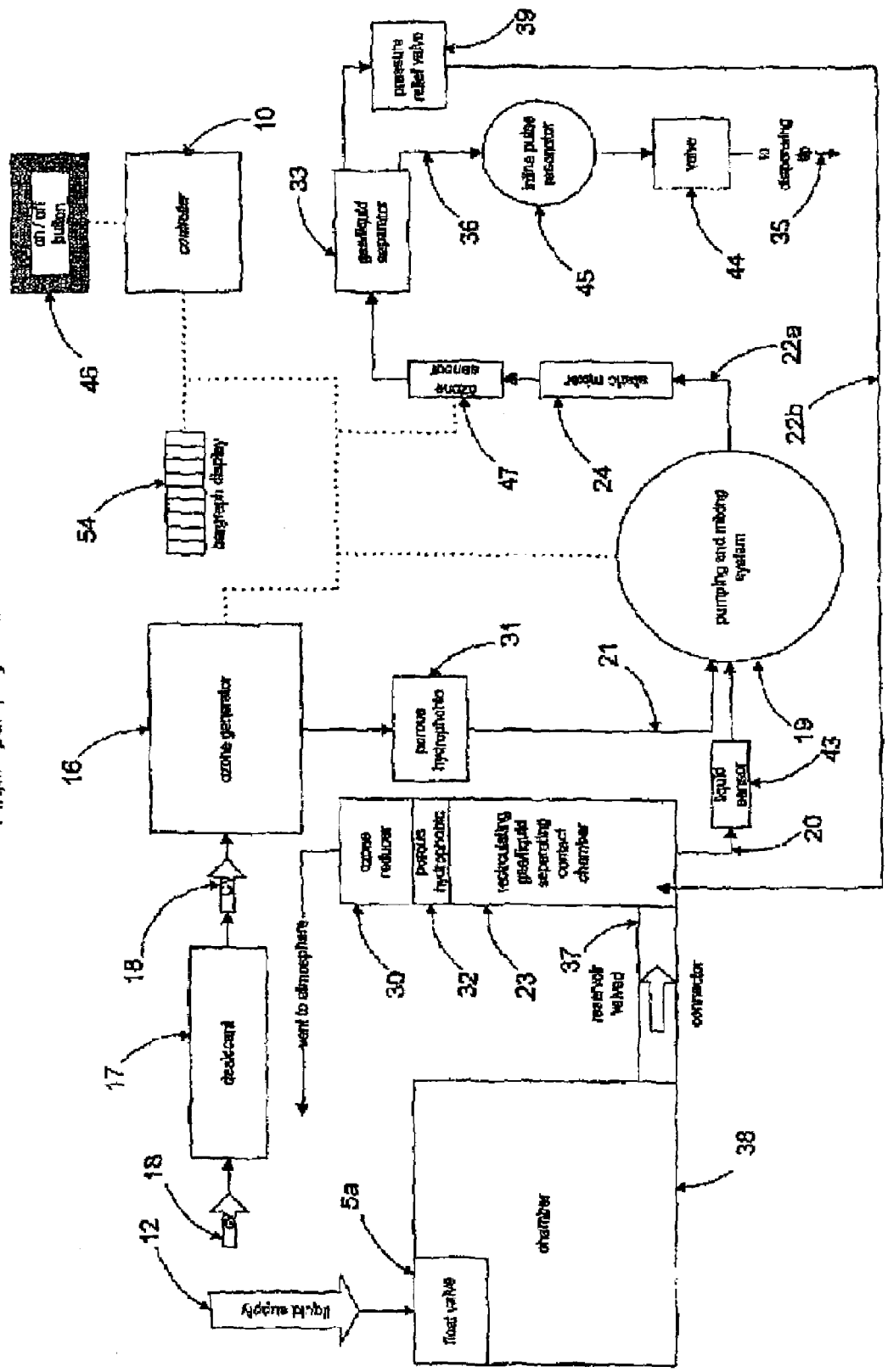

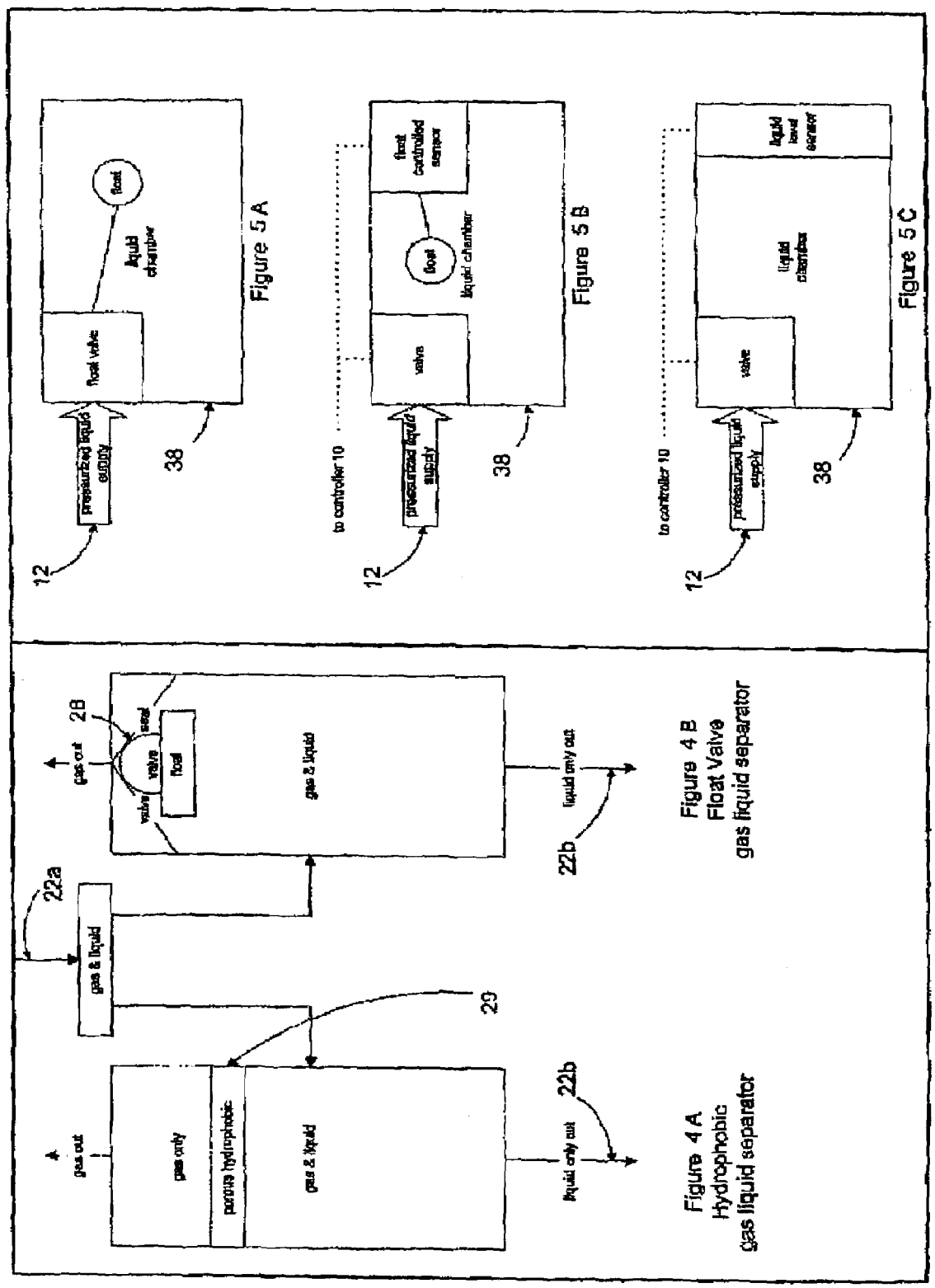

Add On Liquid Pump System

Add On Diffuser System

OZONE IRRIGATOR

This application claims the benefit of U.S. Provisional Application No. 60/261,415, filed on 12 Jan. 2001, which provisional application is incorporated by reference herein.

TECHNICAL FIELD

Our invention pertains generally to ozone generators used for the creation of ozonated fluids. It can be used for a variety of purposes, including oral irrigation devices primarily for home use.

BACKGROUND

By this invention, we have improved upon the portable oral irrigation device. WaterPik™ is a well-known trade name belonging to WaterPik Technologies, Inc. The WaterPik™ is an example of the type of consumer appliance we are improving. By dissolving ozone in the liquid and removing the undissolved gas from the dispensed liquid, we are able to deliver a potent oxidizing liquid to the oral cavity. The benefits of oxidation are known and will be detailed in the summary of the invention. We believe the addition of dissolved ozone to an oral irrigant to be a significant and beneficial improvement to oral irrigators without dissolved ozone. We also believe dissolved ozone to be much more effective at oxidizing oral bacteria than undissolved ozone gas transported to a point of desired disinfection. It also should be noted that an ozone-containing gas potent enough to cause disinfection is known to be offensive to the sense of smell.

SUMMARY OF THE INVENTION

When used as a portable oral care appliance, our invention cleans teeth by liquid (water or solution) irrigation similar to devices presently on the market. Preferably, the cleaning action is enhanced by pulsations of the liquid stream. What is novel is that the water contains dissolved ozone, which is a potent oxidizer and germ killer.

The dissolved ozone can reduce or eliminate gingivitis, gum bleeding, bad breath, teeth stains, and harmful oral bacteria. As well as cleaning teeth and refreshing the mouth, this inexpensive and easy to use small appliance can save users unpleasant and costly dental treatments and make them more attractive with whiter teeth and sweet breath. Reducing oral bacteria may also help prevent some serious diseases such as diabetes and coronary disease in which oral bacteria have been implicated. Potentially, this appliance could also substantially reduce or prevent dental tartar and caries, but this has not yet been confirmed. Other possible applications are nasal irrigation for sinusitis treatment or ear irrigation, eye care, and general home cleaning. In the last application mentioned, it is important to keep in mind the value and benefits of dissolved ozone as an antiseptic cleaner. The ozonated fluids generated by our invention can be used to clean counter tops, vegetables, cutting boards, changing tables, baby toys and other household items. Additionally, since the output pump may be independent of the ozone dissolving system, the ozone dissolving system can be configured as an add on device. Thus, our invention could also be used with an oral irrigator such as a Water Pik™ manufactured by WaterPik Technologies, Inc. In this configuration, the ozonated liquid is delivered by either gravity or pumped flow to the original reservoir connection. Thus, the oral irrigator serves as the delivery portion of the invention when used in this manner.

DRAWINGS

FIG. 3 is a schematic drawing of another alternative embodiment, which can be referred to as a one liquid pump system. This embodiment makes use of only one pump to provide the mixing and dispensing of the ozonated liquid.

FIGS. 4A and 4B are schematic drawings of two different gas/liquid separators.

FIGS. 5A, 5B and 5C are schematic drawings of three different liquid level controls for use when attached to a pressurized liquid supply.

Figure 6:
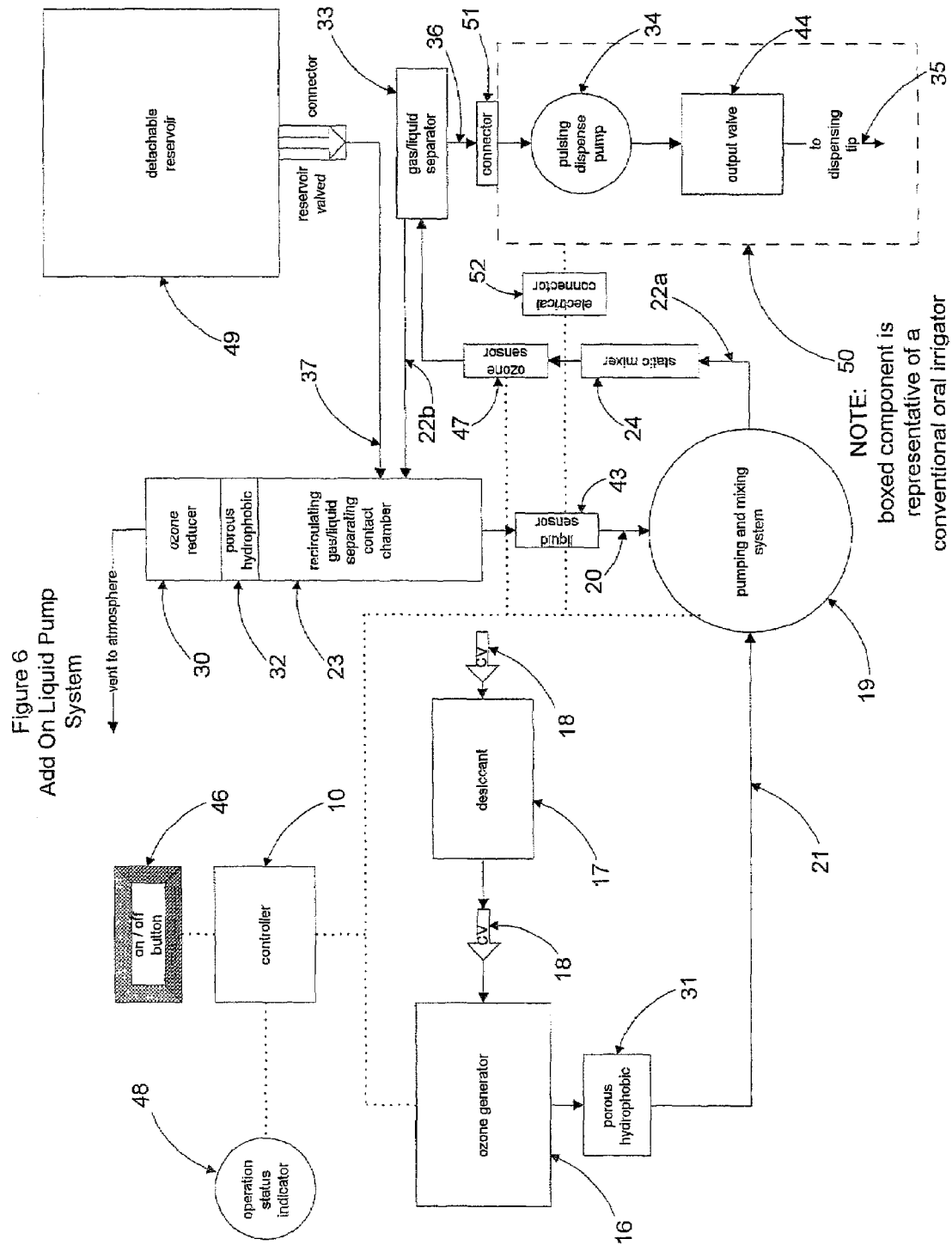

FIG. 6 is a schematic drawing of another alternative embodiment. The system used in this embodiment is similar to that of FIG. 1. The difference is in making use of a conventional non-ozonating oral irrigator to deliver the ozonated liquid.

Figure 7:
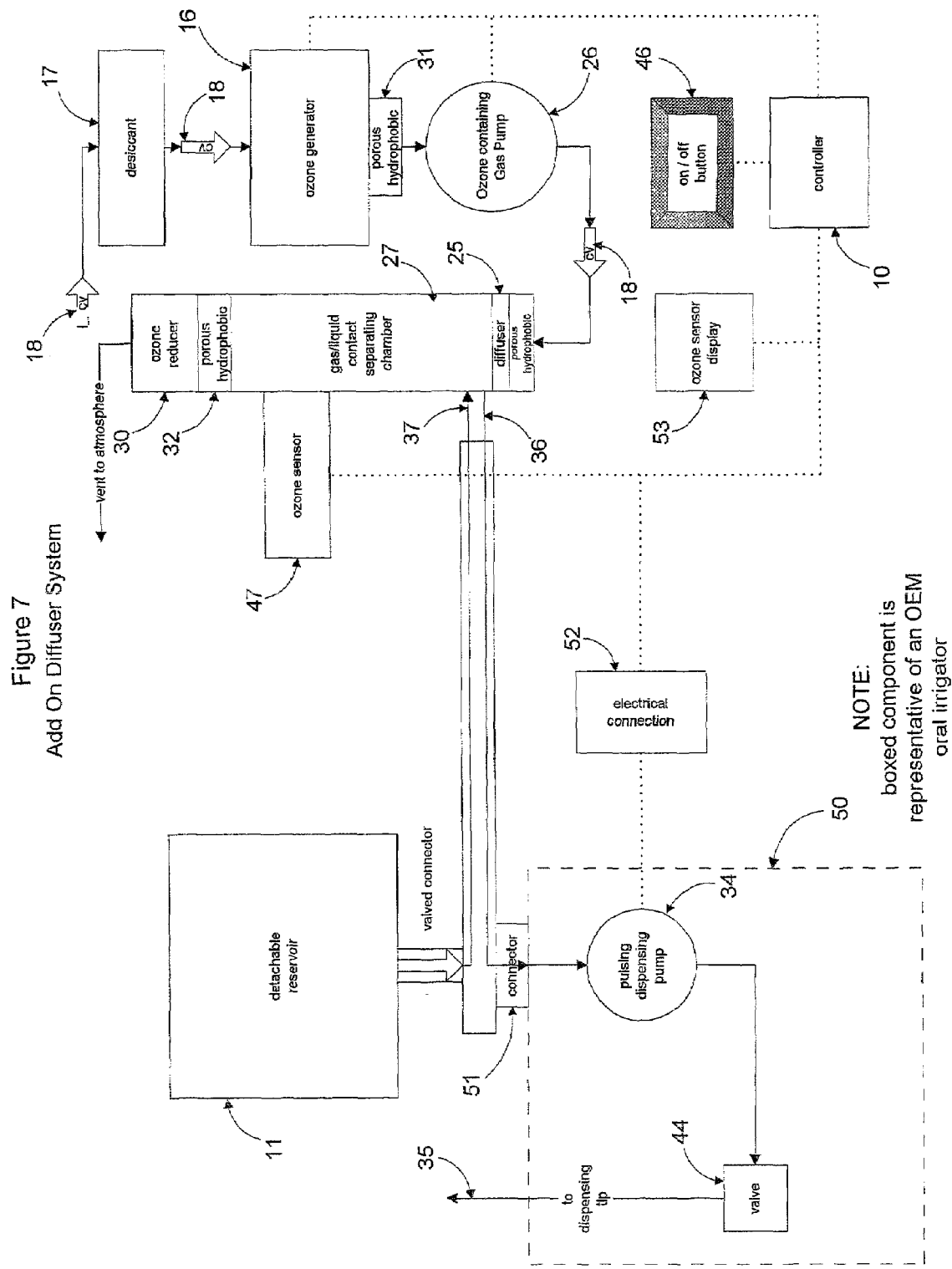

FIG. 7 is a schematic drawing of another alternative embodiment. The system used in this embodiment is similar to that of FIG. 2. Again, the difference is in making use of a conventional non-ozonating oral irrigator to deliver the ozonated liquid.

DETAILED DESCRIPTION

This invention makes possible a small, low-cost, and user-friendly appliance. The water source is preferably a removable refillable reservoir 11, but could be an attachment to a pressurized water supply 12. A pressurized water supply 12 would need a valve as illustrated in FIGS. 5A-5C to regulate incoming water flow. This valve could be a float valve as illustrated in FIG. 5A, a solenoid valve controlled by a float switch as illustrated in FIG. 5B, or a solenoid valve controlled by the system controller 10 responsive to liquid level sensor as illustrated in FIG. 5C.

Figure 1:
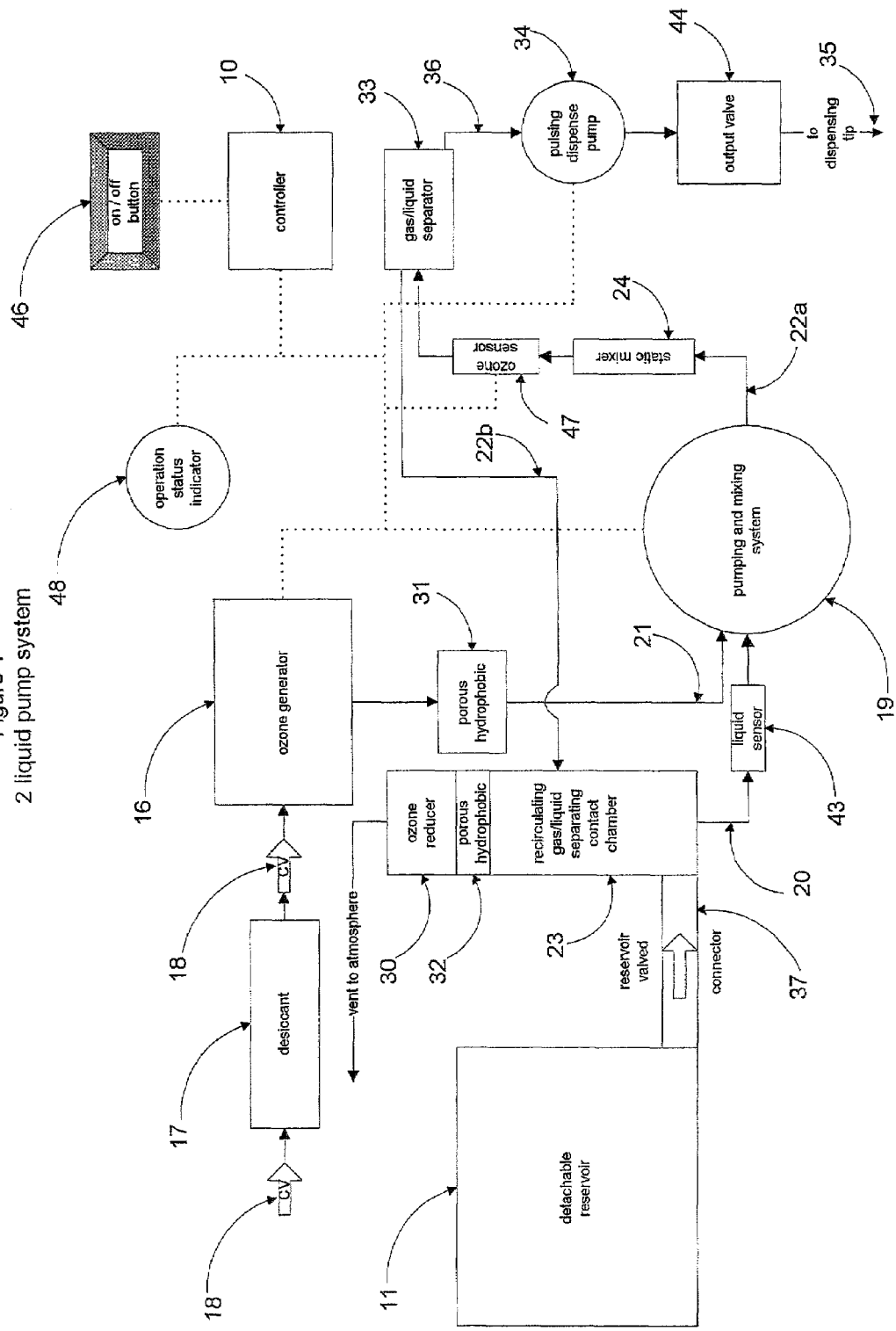
FIG. 1 is a schematic drawing of our preferred embodiment, which can be referred to as a two liquid pump system. One pump is used to pump and mix the ozone gas and liquid and a second pump is used to dispense the ozonated liquid.
Figure 2:
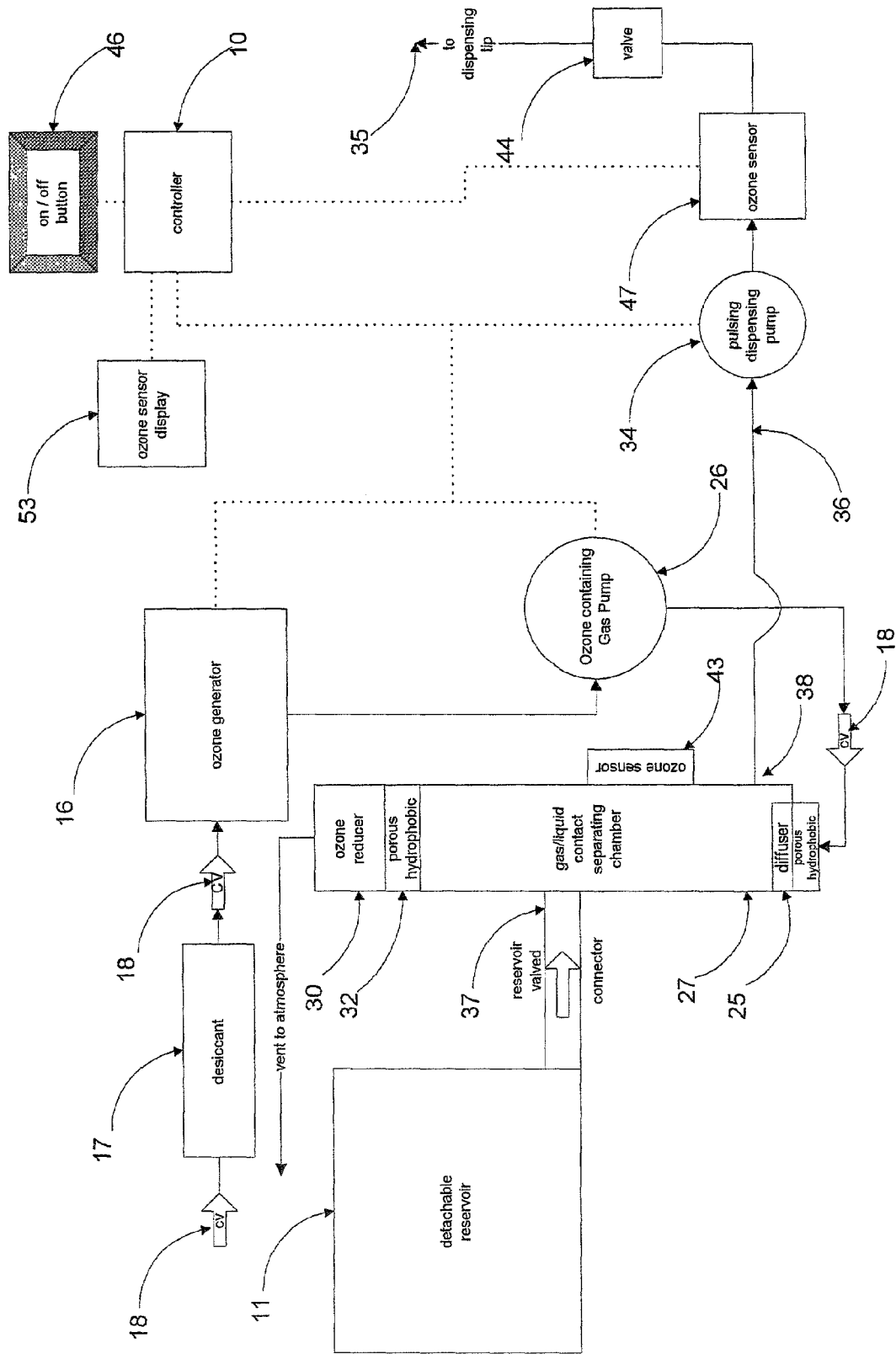
FIG. 2 is a schematic drawing of an alternative embodiment, which can be referred to as a diffuser system using an ozone-containing gas pump and a diffuser to dissolve the ozone in the liquid.

The devices of FIGS. 1-3 generate an ozone containing gas using corona discharge, preferably using the corona discharge generator disclosed in Burris' U.S. Pat. No. 5,529,760. The corona discharge method is preferred over the ultraviolet (UV) method, because it can produce the much higher gas ozone concentration needed to achieve an ozone concentration in the liquid adequate for disinfection. Preferably, the air supplied to the ozone generator 16 is dried by passing through a desiccant material 17. The desiccant material 17 should be protected from moist air when the device is not operating by using spring loaded-check valves 18 on both the entry and exit.

The devices of FIGS. 1 and 2 dissolve the ozone in the liquid by mixing continuously during operation. (See, mixing methods disclosed in Burris' U.S. Pat. Nos. 4,555,335, 5,207,993 and 5,213,773.) Our preferred mixing method is to use a positive pressure pump 19 (such as a piston, rotary vane, diaphragm, or, preferably, a gear pump) in a liquid bypass as illustrated in FIG. 1. In the bypass mixing method, a liquid line 20 from the contact chamber 23 and the line 21 from the ozone generator 16 come together at the pump inlet. The bypass pump 19 mixes the gas and liquid and pumps both through the bypass line 22a and 22b into the treatment chamber 23. Preferably, a static mixer 24 is used between the pump 19 and the contact chamber 23 to assist in dissolving ozone. As shown in FIG. 2, an alternate lower cost dissolving method diffuses the ozone containing gas into the liquid in a treatment chamber 27 through a fine bubble diffuser 25, preferably the diffuser 25 disclosed in Burris' U.S. Pat. Nos. 5,422,043 and 5,858,283. The use of a gas pump 26 rather than a liquid pump 19 for dissolving ozone results in a lower cost.

With a constant flow of ozone containing gas in excess of what can be dissolved, the ozone concentration in the liquid is, in accordance with Henry's law, maintained at the desired level during the operation of the device. One of the great advantages of ozone is that according to Henry's law, the dissolved ozone concentration is determined by the partial pressure of ozone in the gas rather than the amount of ozone so long as there is an excess of ozone. The excess ozone containing gas is separated from the liquid after mixing, preferably by gravity (as illustrated in FIGS. 1-3), using a porous hydrophobic material 29 (as in FIG. 4A), or using a float valve 28 (as in FIG. 4B). The use of a porous hydrophobic material 29, such as polytetrafluoroethylene, eliminates a moving part and thus improves reliability. The separated gas is passed through an ozone reducing material 30 before the gas is released to the atmosphere. Thus, no ozone gas is released from the device to the atmosphere, and bubbles are eliminated from the liquid output line 36 where they might cause problems. The gas/liquid separation is preferably conducted at minimal pressure to reduce the solubility of the gas and the tendency of bubble formation after the liquid is outputted to atmospheric pressure. Liquid is prevented from entering the ozone generator 16, preferably by use of a porous hydrophobic material 31 or a check valve 18. Liquid is prevented from entering the ozone reducing material 30 preferably by use of a porous hydrophobic material 32.

For the pumped bypass mixing system, the preferred arrangement of the outlet line 22a and 22b and gas/liquid separation is a gravity gas/liquid separator 33 in the bypass line. The output pump 34 is connected to the separator 33 at a point where there is only bubble-free liquid. The bypass mixing/circulating pump 19 and the output pump 34 are sized so that the bypass pump 19 always pumps at a greater flow rate than the output pump 34. The liquid which is not pumped out through the dispensing tip 35 and all of the gas is returned to the treatment (contact) chamber 23. Thus, the recirculated ozonated liquid is divided into two streams, one of which is reozonated (at 22b) and the other (at 36) outputted through the dispensing tip 35. The undissolved ozone containing gas is vented from the contact chamber 23 which also separates the gas from the liquid by gravity. Gravity gas/liquid separation desirably works at close to atmospheric pressure. The only pressure is the pressure drop through the porous hydrophobic material 32 and the ozone reducing material 30.

An alternate arrangement would be for the bypass pump 19 to return the gas/liquid mixture directly to the treatment chamber 23, so that the chamber would be the only gas/liquid separator. In this arrangement and the diffuser system of FIG. 2, the untreated replacement liquid entry 37 should be separated from the outlet 38 to the output pump 34.

The liquid supply can be either a pressurized water line 12 or a reservoir 11, which can be refilled or changed when the liquid supply runs low. Referring now to FIGS. 5A-5C, the liquid from a pressurized water line 12 can be admitted to liquid chamber 38. Liquid chamber 38 can be configured as the contact chamber 23 of FIGS. 1 or 3 or treatment chamber 27 of FIG. 2 by a valve 5a, 5b or 5c as needed to replace outputted liquid. Admission of replacement liquid from a reservoir can be controlled by gravity, a float valve, or a pump responsive to the float controlled sensor 5b or liquid level sensor 5c. The ozone containing liquid is pumped out of the dissolving system at the flow rate controlled by, preferably, an output valve 44 or by the pumping rate. Because the output pump 34 of FIGS. 1 and 2 is independent of the ozone dissolving system, changes in the output flow rate do not affect the ozone dissolving system.

Alternately, but not preferably, the ozone pumping and mixing pump 19 could be used both for ozone pumping and mixing and for liquid dispensing through the use of a pressure regulator 39 to provide pressure to dispense as shown in FIG. 3. The advantage of this "straight through" method is lower cost, and the difficulty with this method is scaling. With scaling, as the output flow rate is adjusted by the user, the pump may not pump the proper ratio of gas to liquid. In particular, the pump may not draw enough gas through the ozone generator 16 at low pumping rates. An ozone gas pump 26 could be added to boost gas pressure at the inlet to the liquid pump 19, but then most of the savings disappear and the design is complicated. Gas/liquid separation is more difficult if done under pressure. A straight through system eliminates recirculation. Recirculating and reozonating the liquid has the advantage of requiring a smaller ozone generating and mixing system and providing more holding time to increase germ killing in the liquid.

The technology to produce the pulsations in water flow to enhance the teeth and gum cleaning action of the output liquid stream is well established. For example, the output pump 34 can produce pulsations with a piston or the liquid output can pass through a resonator 45. What we claim in our invention is the combining of conventional oral irrigators 50 with ozonation to produce a stream of preferably pulsating liquid containing dissolved ozone to simultaneously enable the benefits of oral irrigation and ozonated liquid.

Operation of the appliance can be further enhanced by the use of a controller 10. Controller 10 may be responsive to on/off switch 46, ozone sensor 47 and liquid sensor 43. An example of the controller in operation would be as follows. Responding to switch 46, the ozone producing portion of the appliance is activated. In FIGS. 1 and 6 this would be ozone generator 16 and pumping and mixing system 19 and in FIGS. 2 and 7 this would be ozone generator 16 and ozone-containing gas pump 26. When ozone sensor 47 signals the controller that an ozone residual has been achieved, then indicator 48, sensor display 53 or bar-graph display 54 can indicate the presence of dissolved ozone. Controller 10 can then start the dispensing pump 34 of FIGS. 1, 2, 6 and 7 while maintaining the operation of the ozone dissolving section previously described. Note that the dispensing pump 34 of FIGS. 6 and 7 is a component part of irrigator 50.

Referring now to FIGS. 6 and 7, the apparatus of FIG. 6 is essentially the same as the apparatus of the embodiment of FIG. 1 and the apparatus of FIG. 7 is essentially the same as the apparatus of the embodiment of FIG. 2. The significant difference in both cases is the detachability of the ozone system from the dispensing system. In the embodiments of FIGS. 6 and 7 the ozonation system is inserted between or in place of the removable reservoir 49 of traditional oral irrigator 50. In this arrangement the apparatus of FIGS. 6 and 7 supplies ozonated liquid to connector 51 from liquid output line 36. Additionally, an electrical connection 52 can be added to the apparatus of FIGS. 6 and 7 so that controller 10 can operate both the traditional oral irrigator 50 and the ozone systems of the apparatus illustrated in FIGS. 6 and 7. Alternately, the electrical connection 52 can simply be provided as a convenience to minimize the number of electrical cords going to the electric supply receptacle at the point of operation. It must also be noted that the contact chamber 27 of the apparatus of FIG. 7 must be located to provide a gravity feed to ozonated liquid connection 51.

To operate one preferred example of the appliance, the removable reservoir 11 is filled with liquid, typically tap water but also solutions such as isotonic saline can be used, and the reservoir 11 is reconnected to the appliance. Then for dental cleaning and treatment, the jet irrigation tip 35 is placed in the mouth and the on/off button 46 is pressed. The water flow can be adjusted with the hand piece valve 44. Preferably, an ozone sensor 47 in the ozonated liquid line 22a operates an indicator 48 to show that ozone is dissolved in the liquid. Operation of the device can also be indicated with a display of bubbles of the ozone containing gas that could, in addition, enhance the attractiveness of the device to consumers.

We claim:

1. A portable manually operated batch operation device comprising:
    a liquid reservoir containing a batch of liquid to be ozonated;
    a generator producing an ozone containing gas;
    an apparatus for preventing liquid from entering the ozone generator;
    a gas pumping system arranged for causing the ozone-containing gas to flow from the ozone generator to a contact region;
    a controller, responsive to an on/off switch, to operate the ozone generator and the gas pumping system continuously while the device is on;
    a liquid passageway arranged to receive liquid from said reservoir solely under the force of gravity, said liquid passageway conducting liquid from the liquid reservoir to the contact region, where ozone from the ozone-containing gas dissolves in the liquid;
    a system for separating undissolved gas from the liquid containing dissolved ozone;
    a system for preventing ozone in the separated gas from escaping into the atmosphere by passing the separated gas through an ozone reducing material before venting;
    a controllable delivery system, connected to and receiving liquid containing dissolved ozone from the liquid passageway, to direct the liquid containing dissolved ozone to the point of use, where a rate of flow through the controllable delivery system is adjusted by the user; and
    a liquid pumping system arranged for receiving liquid containing dissolved ozone from the contact region and causing the liquid containing dissolved ozone to move through the liquid passageway from the liquid reservoir to the controllable delivery system.

2. The device of claim 1 where a control system is arranged for operating the generator, the liquid passageway, the gas pumping system, and the liquid pumping system.

3. The device of claim 1 wherein the generator is a corona discharge generator.

4. The device of claim 1 where the pumping system uses pump means to mix the ozone-containing gas with the liquid and recirculate the liquid being ozonated until it is dispensed from the device.

5. The device of claim 4 where the pump means includes a static mixer.

6. The device of claim 4 where the pump means is a positive pressure liquid pump.

7. The device of claim 4 where a second pump is used to dispense the ozonated liquid.

8. The device of claim 1 where the ozone containing gas is pumped by a gas pump through a diffuser into the liquid.

9. The device of claim 1 where the generator produces more ozone than can be dissolved in the liquid flow.

10. The device of claim 1 where the dissolved ozone concentration is determined by the solubility of ozone in the liquid.

11. The device of claim 1 where a valve controls the rate of output flow of the ozonated liquid through a dispensing tip.

12. The device of claim 11 where the excess portion of the ozonated liquid flow is recirculated to the contact region or reservoir.

13. The device of claim 12 where the output pressure is regulated by a relief valve in the recirculation line.

14. The device of claim 1 wherein the controllable delivery system further includes a pulsation device to pulsate the liquid as it leaves the controllable delivery system.

15. The device of claim 14 where the pulsation device includes an outputting pump.

16. The device of claim 14 where the pulsation device includes a resonating structure in the liquid output line.

17. The device of claim 1 where porous hydrophobic material is used to prevent liquid from entering the ozone generator.

18. The device of claim 1 where the excess gas is separated from the liquid at minimal pressure.

19. The device of claim 1 where the excess gas is separated from the liquid by use of porous hydrophobic material.

20. The device of claim 1, further including a system which prevents liquid from entering the ozone reducing material.

21. The device of claim 20 where liquid is prevented from entering the ozone reducing material by use of a porous hydrophobic barrier.

22. The device of claim 1 where an ozone sensor causes an indicator to show that the device is operating properly.

23. The device of claim 1 where the liquid reservoir is a reservoir that can be temporarily removed for filling with liquid.

24. The device of claim 1 where bubbles of the ozone containing gas are displayed.

25. The device of claim 1 where the air supplied to the ozone generator is dried by passage through a desiccant material.

26. The device of claim 25 where the desiccant material is protected from entry of moist air when the device is not operating by use of spring loaded check valves.

27. The device of claim 1 where the gas/liquid separating apparatus includes a float valve.

28. The device of claim 1 where the ozone producing and dissolving system and the liquid dispensing system are detachable from one another.

29. The device of claim 28 where the liquid dispensing system is responsive to the controller by means of an electrical connection.

30. The device of claim 1 where the liquid passageway extends to a dispensing tip and where the liquid pumping system is arranged to cause the liquid to move from the contact region to the dispensing tip.

31. A method of dispensing a liquid containing dissolved ozone, comprising:
providing a batch of liquid to be dispensed in a liquid reservoir;
using an ozone generator, producing an ozone-containing gas;
preventing the liquid from entering the ozone generator;
pumping the ozone-containing gas from the ozone generator to a contact region;
conducting liquid from the liquid reservoir to the contact region, where ozone from the ozone-containing gas is dissolved in the liquid to be dispensed;
separating undissolved gas from the liquid to be dispensed;
preventing ozone gas from escaping into the atmosphere by passing the undissolved gas through an ozone reducing material before venting;
pumping a liquid containing dissolved ozone from the contact region and thereby causing the liquid containing dissolved ozone to move through the liquid passageway from the liquid reservoir to a controllable delivery system; and
directing the liquid containing dissolved ozone to the point of use, where the rate of flow through the controllable delivery system is adjustable.

32. The device of claim 1, wherein said liquid reservoir comprises a detachable reservoir.

* * * * *